US010631751B2

(12) United States Patent
Miyazaki et al.

(10) Patent No.: US 10,631,751 B2
(45) Date of Patent: Apr. 28, 2020

(54) MOTION ANALYSIS APPARATUS, METHOD FOR ANALYZING MOTION, AND MOTION ANALYSIS PROGRAM

(71) Applicant: Osaka University, Osaka (JP)

(72) Inventors: Fumio Miyazaki, Osaka (JP); Hiroaki Hirai, Osaka (JP); Mitsunori Uemura, Osaka (JP); Kanna Uno, Osaka (JP); Takanori Oku, Osaka (JP)

(73) Assignee: Osaka University (JP)

( * ) Notice: Subject to any disclaimer, the term of this patent is extended or adjusted under 35 U.S.C. 154(b) by 882 days.

(21) Appl. No.: 15/104,655

(22) PCT Filed: Nov. 20, 2014

(86) PCT No.: PCT/JP2014/080764
§ 371 (c)(1),
(2) Date: Jun. 16, 2016

(87) PCT Pub. No.: WO2015/093224
PCT Pub. Date: Jun. 25, 2015

(65) Prior Publication Data
US 2016/0324436 A1    Nov. 10, 2016

(30) Foreign Application Priority Data

Dec. 16, 2013  (JP) .................................. 2013-259093

(51) Int. Cl.
*A61B 5/0488*  (2006.01)
*A61B 5/11*  (2006.01)
(Continued)

(52) U.S. Cl.
CPC .......... *A61B 5/0488* (2013.01); *A61B 5/1122* (2013.01); *A61B 5/1124* (2013.01);
(Continued)

(58) Field of Classification Search
CPC ... A61B 5/0488; A61B 5/1122; A61B 5/1124; A61B 5/1128; A61B 5/22; A61B 5/4058; A61B 5/4076
(Continued)

(56) References Cited

U.S. PATENT DOCUMENTS

2004/0138583 A1* 7/2004 Galea .................... A61B 5/0488
600/547
2007/0172797 A1* 7/2007 Hada ...................... G09B 23/32
434/1
(Continued)

FOREIGN PATENT DOCUMENTS

| JP | 2004-073386 | 3/2004 |
|---|---|---|
| JP | 2009-543649 | 12/2009 |
| WO | WO-2011/030781 | 3/2011 |

OTHER PUBLICATIONS

Kanna Uno et al., "Estimation of Hand Stiffness and Equilibrium Point Using EMG for Human Motion Visualization", Proceedings of the 2013 JSME Conference on Robotics and Mechatronics, No. 13-2, Tsukuba, Japan May 22-25, 2013, pp. 2A1-G03(1)-(4).
(Continued)

*Primary Examiner* — Daniel L Cerioni
(74) *Attorney, Agent, or Firm* — Jordan and Koda, PLLC

(57) ABSTRACT

In order to estimate a movement command that a central nervous system is to select to implement a desired movement based on three feature amounts under the concepts of an antagonistic muscle ratio and an antagonistic muscle sum and based on a musculoskeletal model, a movement analysis apparatus includes: a myoelectric potential measurement unit to measure a myoelectric potential of a person who performs a movement; a movement measurement unit to measure a body movement; and a stiffness-ellipse calculation unit, an equilibrium-point calculation unit and a muscle synergy calculation unit to calculate, from measurement
(Continued)

information obtained at the measurement units, feature amounts of a stiffness ellipse, an equilibrium point, and a muscle synergy that are base vectors describing the equilibrium point at an operating point based on a musculoskeletal model.

7 Claims, 13 Drawing Sheets

(51) Int. Cl.
 *A61B 5/22* (2006.01)
 *A61B 5/00* (2006.01)
(52) U.S. Cl.
 CPC .............. *A61B 5/1128* (2013.01); *A61B 5/22* (2013.01); *A61B 5/4058* (2013.01); *A61B 5/4076* (2013.01); *A61B 5/4528* (2013.01); *A61B 2503/10* (2013.01)
(58) Field of Classification Search
 USPC ........................................................ 600/595
 See application file for complete search history.

(56) References Cited

U.S. PATENT DOCUMENTS

2011/0054870 A1* 3/2011 Dariush .................. G06F 3/011
 703/11
2012/0172745 A1* 7/2012 Miyazaki ............. A61B 5/0488
 600/546

OTHER PUBLICATIONS

Kanna Uno et al., "Tayo na Hito Joshi Undo-kan de Kyotsu sura Kin Kyocho Pattern no Chushutsu", Annual Conference of the Robotics Society of Japan Yokoshu, vol. 31st, Sep. 4, 2013 (Sep. 4, 2013), ROMBUNNO.2F2-03.
Hiroaki Gomi and Mittsuo Kawato, "Equillibrium-Point Control Hypothesis Examined by Measured Arm Stiffness During Multijoint Movement," Science, vol. 272, No. 5258, pp. 117-120, 1996.
Hiroaki Gomi and Mitsuo Kawato, "Measurement of Mechanical Impedance of Human Arm during Multijoint Movement in Horizontal Plane", Transactions of the Society of Instrument and Control Engineers, vol. 32, No. 3, pp. 369-378, 1996.

* cited by examiner m1: DELTOID POSTERIOR
m2: DELTOID ANTERIOR
m3: TRICEPS LONG HEAD
m4: BICEPS
m5: TRICEPS LATERAL HEAD
m6: BRACHIORADIALIS

Fig. 3

| label | definition | function |
|---|---|---|
| $r_1$ | $\frac{m_1}{m_1+m_2}$ | shoulder-joint angle extension |
| $r_2$ | $\frac{m_3}{m_3+m_4}$ | shoulder & elbow-joint angle extension |
| $r_3$ | $\frac{m_5}{m_5+m_6}$ | elbow-joint angle extension |
| $s_1$ | $m_1 + m_2$ | shoulder-joint stiffness increase |
| $s_2$ | $m_3 + m_4$ | shoulder & elbow-joint stiffness increase |
| $s_3$ | $m_5 + m_6$ | elbow-joint stiffness increase |

Definitions and functions of antagonistic muscle ratio r_i (i=1,2,3) (A-A ratio) and antagonistic muscle sum s_i (i=1,2,3) (A-A sum)

PLANE π WHERE ANTAGONISTIC
MUSCLE RATIO CAN CONTRIBUTE TO
MOVEMENT OF OPERATING POINT

Fig. 9A
Fig. 9B
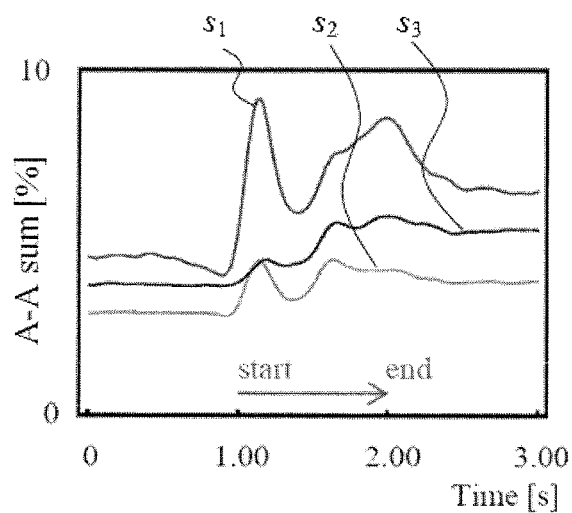
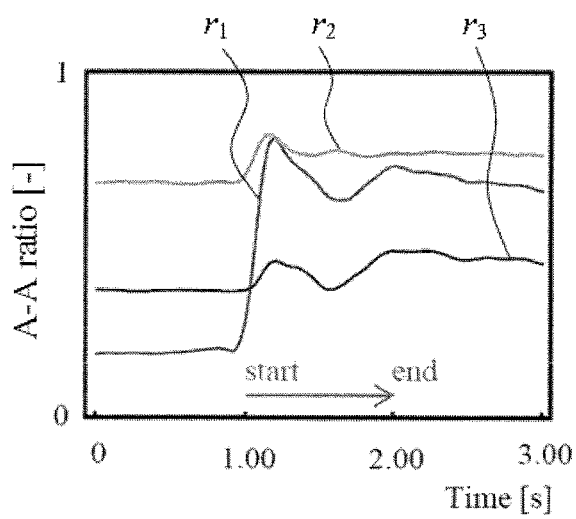
Antagonistic muscle sum (A-A sum)
and Antagonistic muscle ratio (A-A ratio) (Subject A)

Fig. 10A Subject A
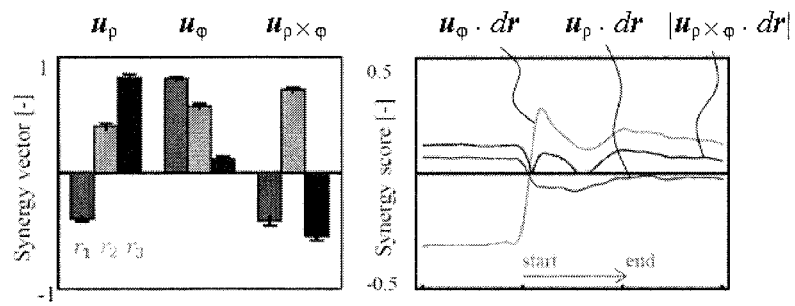
Fig. 10B Subject B
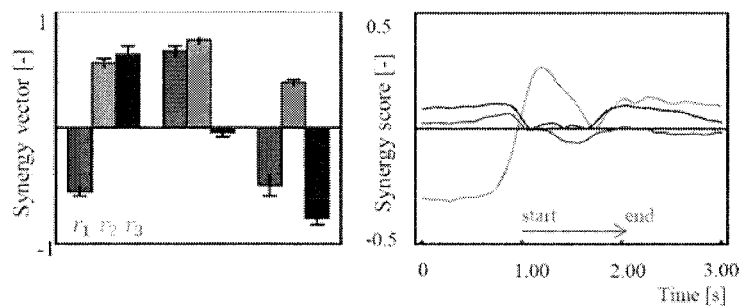
Extracted muscle synergies: (left) muscle synegy vectors $u_\rho$, $u_\varphi$ and $u_{\rho \times \varphi}$; (right) muscle synergy scores.

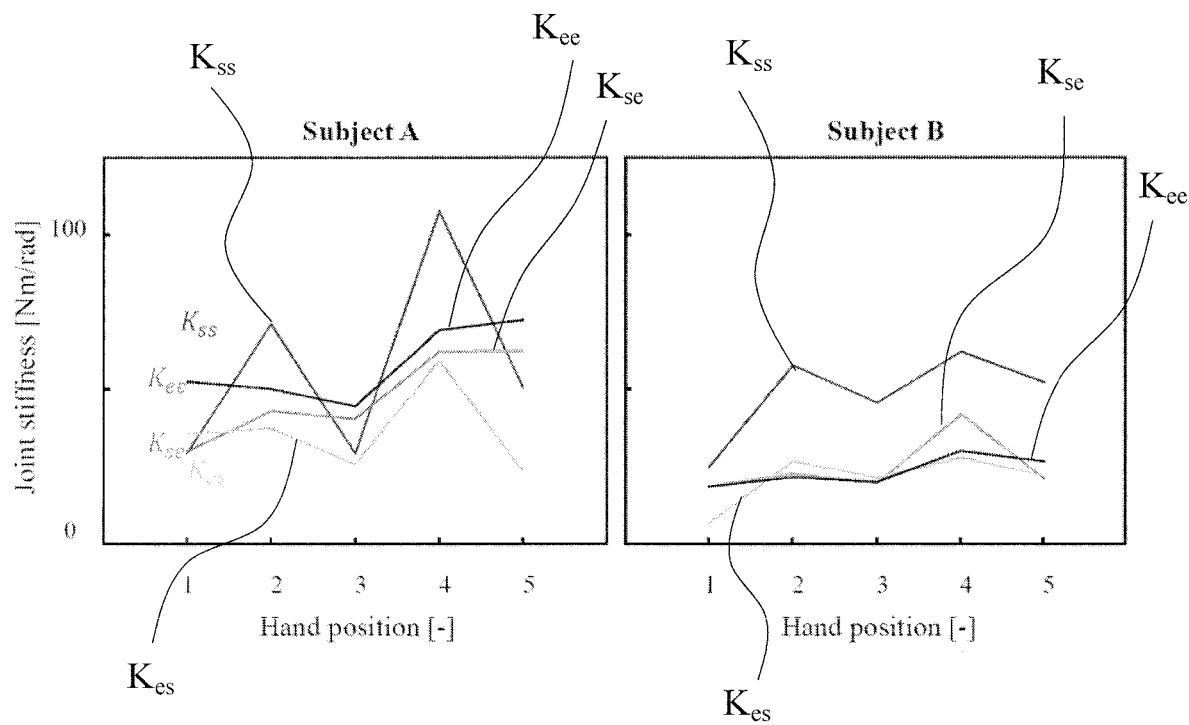
Joint stiffness estimated by using robotic perturbations.

Stiffness ellipse (subject A): (A) hand stiffness estimated by using robotic perturbations; (B) hand stiffness estimated by muscle synergy analysis with antagonistic muscle sum (A-A sum) and null synergy score; (C) hand stiffness estimated by muscle synergy analysis with A-A sum only.

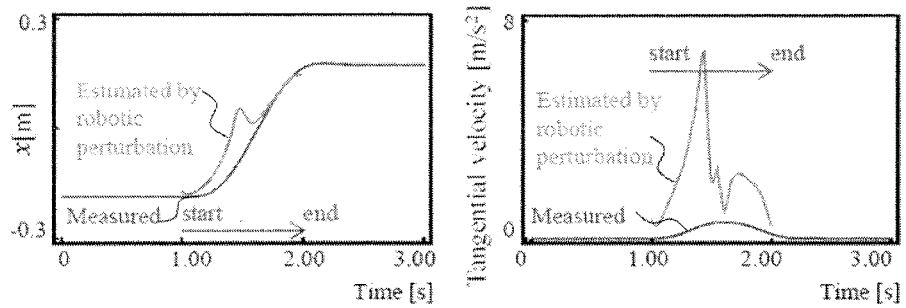
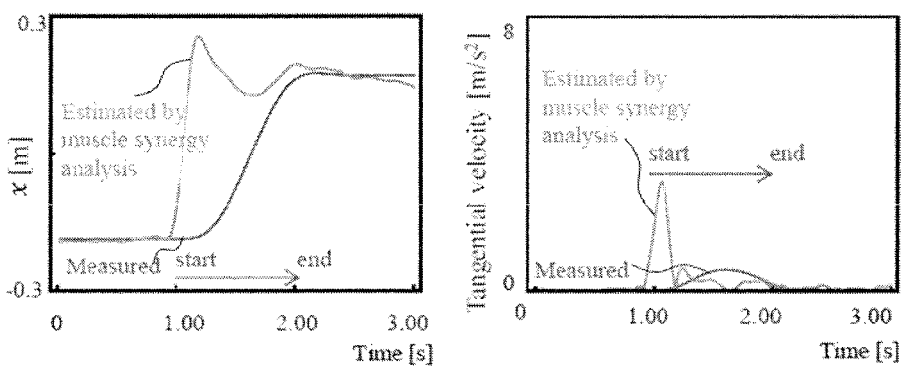
Hand trajectory and EP trajectory (subject A):
(A) estimation by using robotic perturbations; (B) estimation by muscle synergy analysis;
The left-side graph shows the position in x direction, and the right-side graph shows its tangential velocity.

MOTION ANALYSIS APPARATUS, METHOD FOR ANALYZING MOTION, AND MOTION ANALYSIS PROGRAM

TECHNICAL FIELD

The present invention relates to a movement analysis technique of calculating a feature amount relating to movement control for an operating point at a suitable part of a body, e.g., at an endpoint of limbs.

BACKGROUND OF THE INVENTION

For effective practice during learning of movement skills, for example, it is desirable to correctly determine the learning level of a learner, and provide them with high-quality information. An operating point directly relating to the implementation of a movement contains rich information for movement evaluation and movement-learning support, and studies on the impedance characteristics and the equilibrium-point trajectory for a target movement have been conventionally performed. Currently proposed methods to estimate these feature amounts include a method of giving perturbations to a target movement, and analyze a variation thereof based on a body model (Non-Patent Literatures 1, 2) and a method of measuring a muscle-group action, kinematics and a hand-force during a target movement, and identifying a model to describe the relationship among them, thus estimating the two feature amounts as stated above (Patent Literature 1). Another method proposed is to analyze the impedance at an operating point and the muscle-group action relating to the implementation of an equilibrium point by a statistical method, and break down them into the units of functions (muscle synergies) to implement the movement (Patent Literature 2).

CITATION LIST

Patent Literature

Patent Literature 1: Patent Application Publication No. 2004-73386
Patent Literature 2: WO2011/030781

Non Patent Literature

Non Patent Literature 1: Hiroaki Gomi and Mitsuo Kawato, "Equilibrium-Point Control Hypothesis Examined by Measured Arm Stiffness During Multijoint Movement," Science, vol. 272, no. 5258, pp. 117-120, 1996.
Non Patent Literature 2: Hiroaki Gomi and Mitsuo Kawato, "Measurement of Mechanical Impedance of Human Arm during Multijoint Movement in Horizontal Plane", Transactions of the Society of Instrument and Control Engineers, vol. 32, no. 3, pp. 369-378, 1996.

SUMMARY OF THE INVENTION

Non Patent Literatures 1, 2 describe a method of estimating the impedance at an operating point and the equilibrium point at an operating point. Such a method, however, requires a high-precision robot and such a device to measure a movement. This means technical problems such that the device becomes large in scale, the movement tasks that can be measured are limited, and perturbations affect a reflex system. Further these literatures do not describe muscle synergies.

Patent Literature 1 requires the collection and analysis of a huge amount of data to create a model, and further when the estimation is performed using a neural-network model, the physical significance thereof is not clear unfortunately. This literature also does not describe muscle synergies. Patent Literature 2 describes impedance, an equilibrium point and muscle synergies, but the muscle synergies extracted have the physical significance that is limited to suggestion based on statistical data. This literature does not describe a stiffness ellipse.

In view of the above, the present invention aims to provide a movement analysis apparatus, a method for analyzing a movement, and a movement analysis program capable of obtaining three feature amounts of a stiffness ellipse, an equilibrium point and base vectors (muscle synergy) describing the equilibrium point at an operating point with a simpler calculation and analytically by considering a body movement as a mechanical system made up of a musculoskeletal structure and introducing the concepts of an antagonistic muscle ratio and an antagonistic muscle sum.

A movement analysis apparatus according to the present invention includes: a measurement unit to periodically measure a muscle-group activity and a body movement of a person who performs a movement; and calculation means to calculate, from measurement information obtained by the measurement unit, feature amounts including a stiffness ellipse, an equilibrium point, and a muscle synergy that is base vectors describing the equilibrium point at an operating point based on a musculoskeletal model.

A method of analyzing a movement according to the present invention includes: periodically measuring a muscle-group activity and a body movement of a person who performs a movement by a measurement unit; and calculating, from measurement information obtained by the measurement unit, feature amounts including a stiffness ellipse, an equilibrium point, and a muscle synergy that is base vectors describing the equilibrium point at an operating point based on a musculoskeletal model.

A movement analysis program according to the present invention makes a computer function as: measurement processing means to fetch information on a muscle-group activity and a body movement of a person who performs a movement that is measured periodically by the measurement unit; and calculation means to calculate, from information obtained by the measurement processing means, feature amounts including a stiffness ellipse, an equilibrium point, and a muscle synergy that is base vectors describing the equilibrium point at an operating point based on a musculoskeletal model.

According to these forms of the invention, a muscle-group activity and a body movement of a person who performs a movement can be measured periodically by the measurement unit, and three feature amounts including a stiffness ellipse, an equilibrium point, and a muscle synergy that is base vectors describing the equilibrium point at an operating point can be calculated from measurement information obtained and based on a musculoskeletal model. These three feature amounts can be obtained in real time through algebraic calculations based on information on the muscle-group activity, the body movement and the musculoskeletal model. The calculation result may be stored once or may be read in real time as needed for use.

Therefore, the feature amounts can be estimated based on a physical model and analytically, can be estimated through algebraic calculations that do not require complicated parameter identification or a large scale apparatus, and can be dealt with uniformly under the concepts of the antagonistic muscle ratio and the antagonistic muscle sum.

The three feature amounts including muscle synergies estimated can be estimated based on a physical model, and therefore the physical significance thereof can be clarified as compared with the one estimated from a neural network model or by a statistical method.

According to the present invention, a motor command selected by a central nervous system to implement a desired movement can be estimated from three feature amounts under the concepts of an antagonistic muscle ratio and an antagonistic muscle sum and based on a musculoskeletal model.

BRIEF DESCRIPTION OF THE DRAWINGS

FIG. 2A shows one example of a movement of the body using an upper limb, and FIG. 2B shows the definition of muscles making up a musculoskeletal model of an upper limb and the coordinate system.

FIG. 3 shows antagonistic muscle ratio, antagonistic muscle sum, and their functions.

FIGS. 9A and 9B show the transition of the antagonistic muscle sum and the antagonistic muscle ratio obtained from the experiment on Subject A, where FIG. 9A shows the antagonistic muscle sum and FIG. 9B shows the antagonistic muscle ratio.

FIGS. 10A and 10B show synergy vectors in the radial, in the deflection-angle and in the Null directions, and their synergy scores, where FIG. 10A shows data on Subject A and FIG. 10B shows data on Subject B.

FIGS. 11A and 11B show characteristic indicating joint stiffness calculated by a perturbation method, where FIG. 11A shows data on Subject A, and FIG. 1 shows data on Subject B.

FIG. 12A shows the data obtained by the perturbation method, and FIG. 12B shows the data obtained by the estimation method this time, and FIG. 12C shows the data obtained without adding the synergy scores in the Null direction.

FIGS. 13A and 13B show the equilibrium-point trajectory of the hand calculated based on the hand stiffness, the equilibrium-point trajectory of the hand estimated from the muscle synergy scores, and the magnitude of their tangential velocities, where FIG. 13A shows the data obtained by the perturbation method, and FIG. 13B shows the data obtained by the estimation method this time.

DESCRIPTION OF THE PREFERRED EMBODIMENTS

Figure 1:
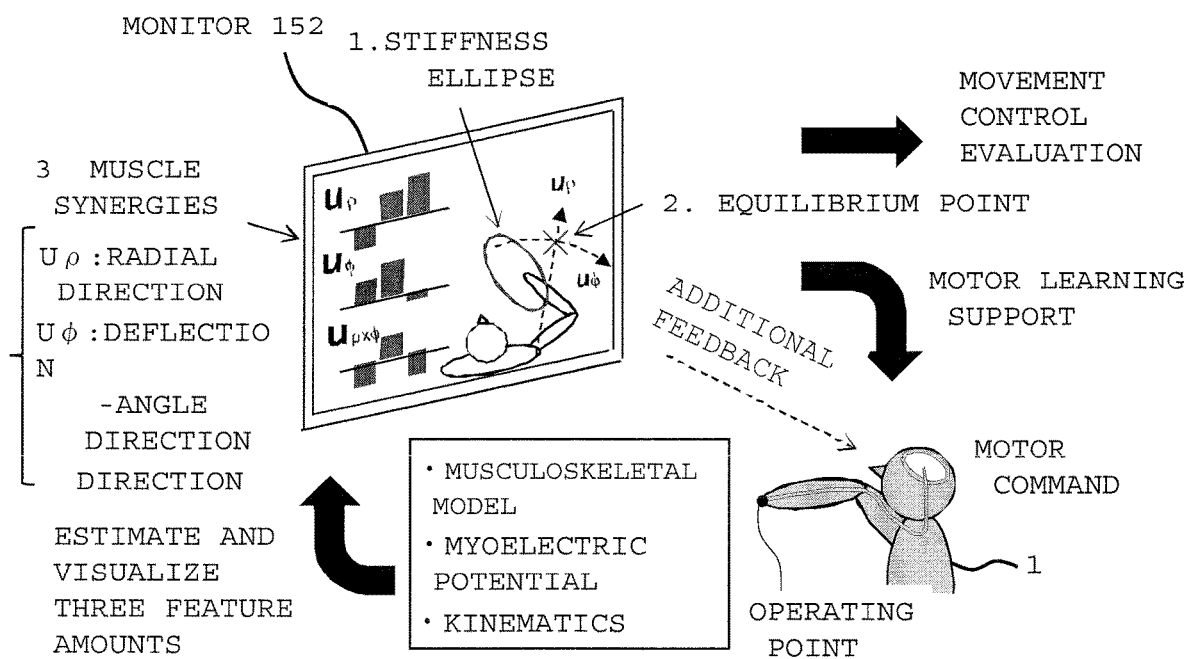
FIG. 1 describes the outline and a usage form of a movement analysis method according to the present invention.
Figure 2A:
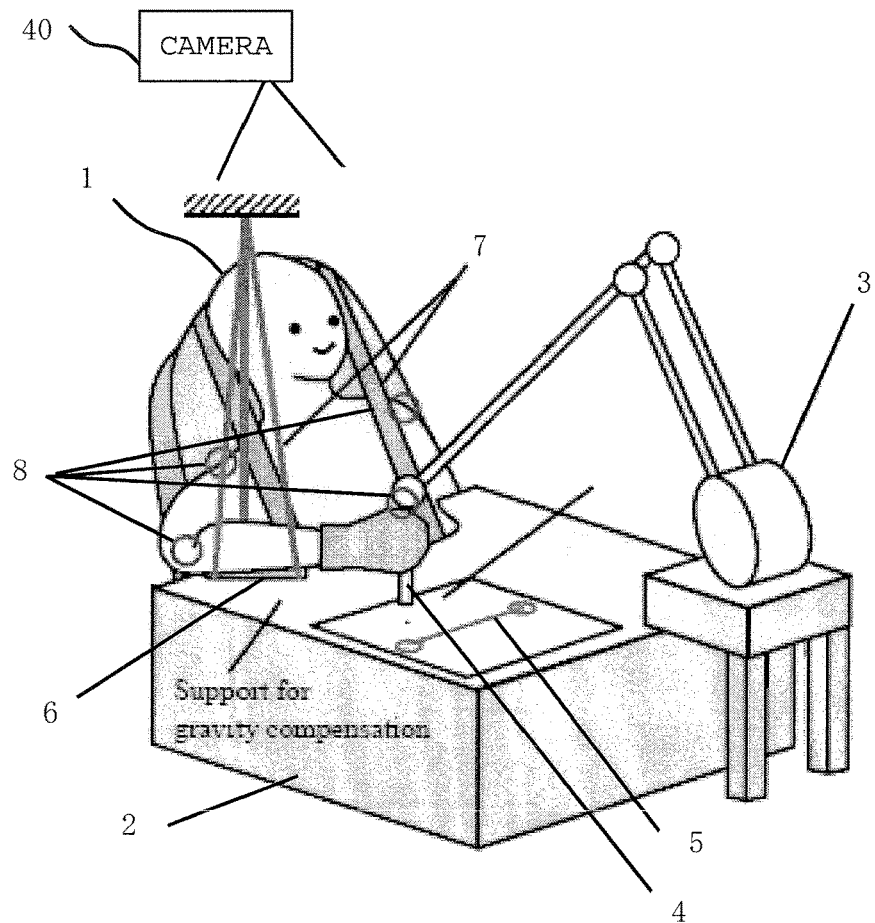
FIGS. 2A and 2B describe one example of a method for analyzing a movement of the present invention, where
Figure 2B:
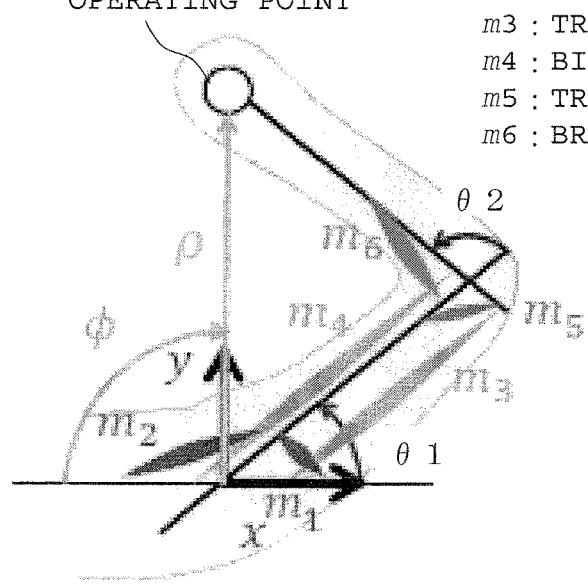
Figure 4:
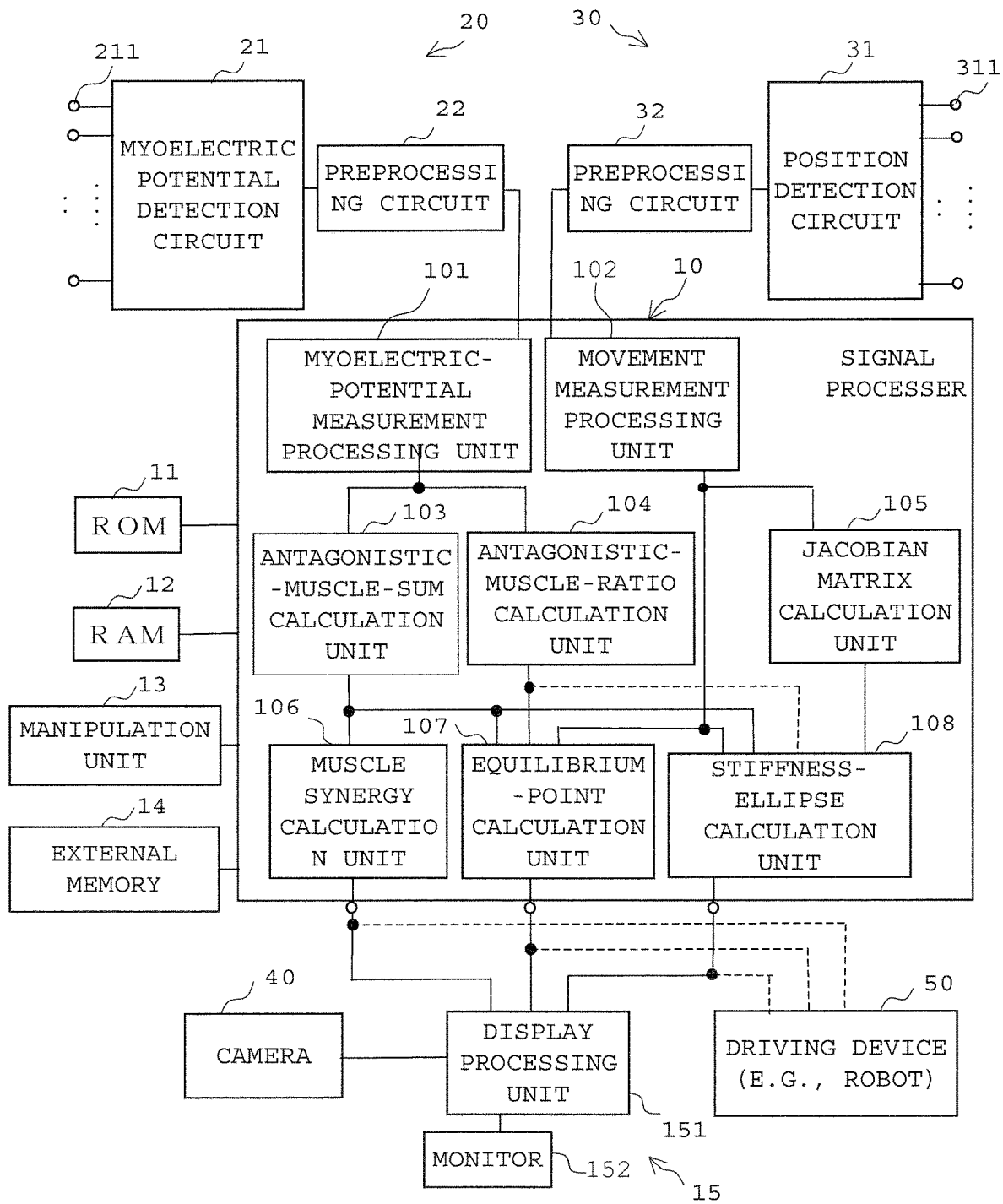
FIG. 4 is a block diagram showing one embodiment of a movement analysis apparatus according to the present invention.
Figure 5:
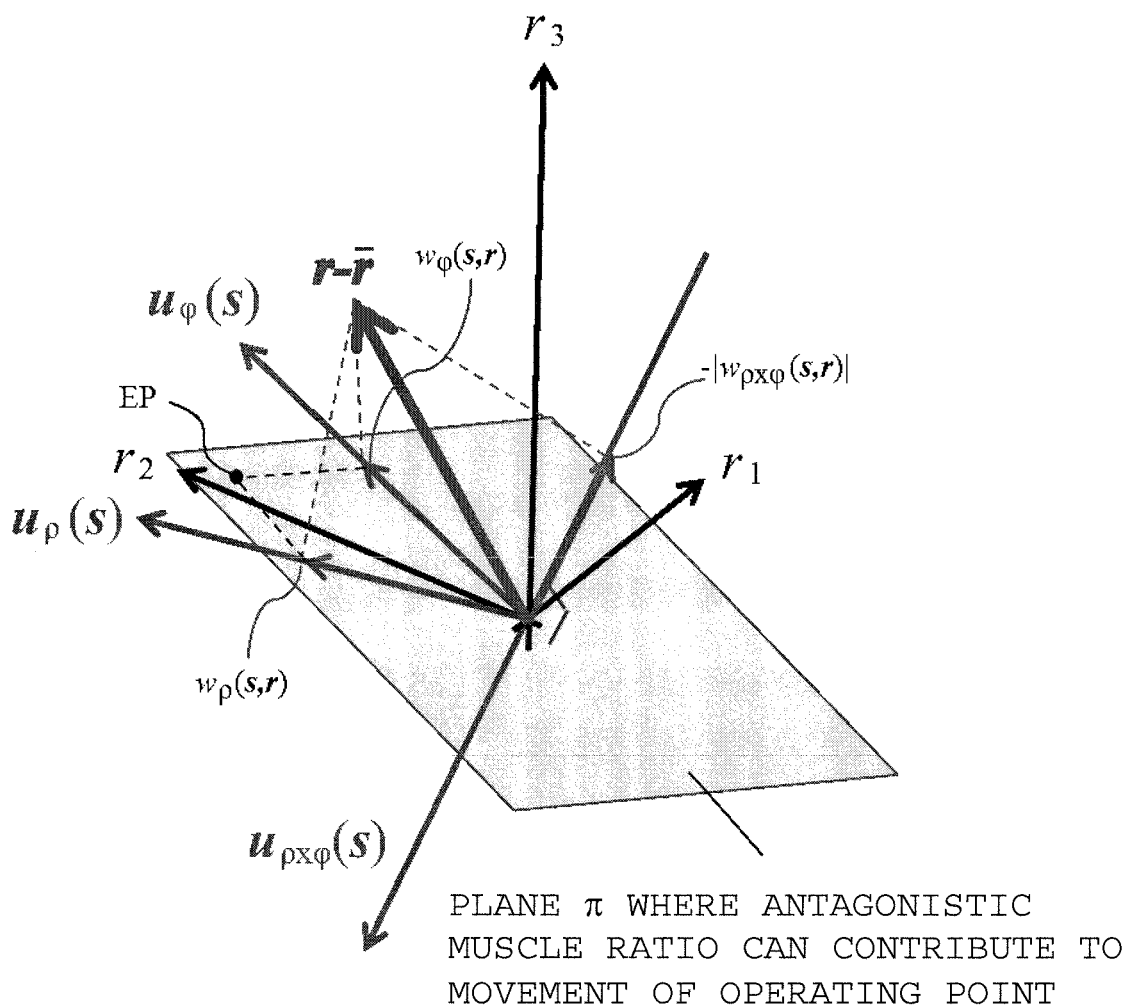
FIG. 5 describes a method for calculating an equilibrium point geometrically.

FIG. 1 describes the outline and a usage form of a movement analysis method according to the present invention. FIGS. 2A and 2B describe one example of a method for analyzing a movement of the present invention, where FIG. 2A shows one example of a movement of the body using an upper limb, and FIG. 2B shows the definition of muscles making up a musculoskeletal model of an upper limb and the coordinate system. FIG. 3 shows antagonistic muscle ratios, antagonistic muscle sums, and their functions. FIG. 4 is a block diagram showing one embodiment of a movement analysis apparatus according to the present invention.

In FIG. 1, a person 1 performs a movement in accordance with a motor command from the central nervous system. Herein, the movement by the person 1 is dealt with as a mechanical system (musculoskeletal model) of a musculoskeletal structure. Preferably information on the musculoskeletal model is stored in the apparatus beforehand. A movement by the person 1 is measured in terms of myoelectric potential and a body movement (kinematics). As a result, a musculoskeletal model, myoelectric potential and kinematics are obtained as the information on the person 1. Three feature amounts are estimated and calculated based on such information, which are then displayed (visualized) on a monitor 152.

The three feature amounts include a stiffness ellipse, an equilibrium point and a muscle synergy that is the base vectors describing the equilibrium point. An image of the movement status by the person 1 is taken, and the image taken is displayed on the monitor 152. The stiffness ellipse is shown around (corresponding to) the operating point, and the equilibrium point is displayed with a dot-like predetermined mark in accordance with the coordinate system of the taken image. The stiffness ellipse is to specify the mobility difficulty (easiness) against postural perturbations at the operating point, which is represented with the direction from the center and the length of the radius. The equilibrium point represents the motor command for positioning the operating point. The muscle synergy in the present embodiment is described with components in the deflection-angle direction, the radial direction and the Null direction (zero direction) orthogonal to them.

The three feature amounts are displayed on the monitor 152, which can offer a movement evaluation on the movement status by the person 1. This also can offer movement-learning support so as to improve the movement status by the person 1.

In FIG. 2A, the person 1 (subject) is sitting on the chair so that the right shoulder is located in front of a manipulator 3 over a desk 2, where both of the shoulders are fixed to the backrest of the chair. The muscles to be examined are three-paired six muscles (one pair of them is a bi-articular muscle pair) playing a major role in the upper-limb movement in a horizontal plane, and the definition of the muscles to be examined and the coordinate system are shown in FIG. 2B. The forearm and the upper arm are suspended from the ceiling with a suspender 6 or are supported from the below so as to be slidable on the desk, whereby influences from the gravity are canceled. In this example, the wrist joint of the right arm is fixed with a cast made of plastic, and a laser pointer 4 directed downward and the forward end of the manipulator 3 are fixed to the hand (operating point). On the desk 2, a sheet 5 is placed, on which the direction and the distance of the movement are shown, so as to allow the subject to visually check the position of the hand with the laser pointer 4 in real time. A camera 40 as an imaging unit is provided above so as to take a movement image, and an image of the movement part at least is taken. Markers 8 for an optical tracking system, such as movement, are fixed at predetermined positions, such as the center of joints of the left shoulder, the right shoulder and the right elbow and immediately above the laser pointer 4 at the right hand. Each marker 8 is detected by a movement detection unit 30 (see FIG. 4) as described later.

FIG. 2B shows the x-y coordinate system with reference to the right shoulder, where ρ denotes the distance from the right shoulder and φ denotes the angle. θ1 and θ2 as kinematics data are measured by the optical tracking system, representing the joint angle at the shoulder joint and the joint angle at the elbow joint, respectively.

As shown in FIG. 2B, the muscles of the upper limb include deltoid posterior m1, deltoid anterior m2, triceps long head m3, biceps m4, triceps lateral head m5 and brachioradialis m6, where m1 and m2, m3 and m4, and m5 and m6 are pairs of antagonistic muscles. As shown in FIG. 3, when mi (i=1 to 6) is considered as myoelectric potentials, the antagonistic muscle sum and the antagonistic muscle ratio are calculated as in Mathematical Expressions (1) and (2).

[Mathematical 1]

< Pre-preparation > (1)

1. Antagonistic muscle sum (A-A sum)

$s_i = m_{2i-1} + m_{2i}$ $(i = 1, 2, 3)$ $s = (s_1, s_2, s_3)^T$

2. Antagonistic muscle ratio (A-A ratio) (2)

$r_i = \frac{m_{2i-1}}{m_{2i-1} + m_{2i}} (i = 1, 2, 3)$ $r = (r_1, r_2, r_3)^T$ 3. Jacobian matrix (3)

$x = (x, y)^T$ $\theta = (\theta_1, \theta_2)^T$ $\dot{x} = J_x(\theta)\dot{\theta}$ $J_x(\theta) = \frac{\partial x}{\partial \theta^T}$ Myoelectric potentials are obtained through the measurement of EMG (electromyogram to directly measure a muscle activity), into which the concept of a ratio (antagonistic muscle ratio) of activities between antagonistic muscles that is considered as a minimum unit for muscle coordination and the concept of a sum (antagonistic muscle sum) of activities of antagonistic muscles are introduced. Myoelectric potentials are represented by percentage % MVC with reference to the myoelectric potential at the isometric maximum voluntary contraction (MVC) for normalization among the muscles.

In FIG. 4, a movement analysis apparatus includes: a myoelectric potential measurement unit 20 to detect a myoelectric potential of the person 1; a movement measurement unit 30 to detect the markers 8 attached to the person 1 so as to measure the joint angles θ1 and θ2 that are kinematics data; and a signal processing unit 10 made up of a computer or the like, which is typically a microcomputer, to perform predetermined signal processing based on the measured myoelectric potentials and joint angles.

The myoelectric potential measurement unit 20 includes a required number of electrodes 211, a myoelectric potential detection circuit 21 to detect electrical signals generated at the electrodes 211, and a preprocessing circuit 22 to perform predetermined preprocessing to the detected electrical signals. The electrodes 211 in this example are to detect myoelectric potentials at the muscles m1 to m6. The myoelectric-potential signals obtained at the body surface are AC signals of a few tens of μV to a few hundreds of μV in level and about 5 [Hz] to 500 [Hz] in frequency. Then, the preprocessing circuit 22 includes an amplifier to amplify the myoelectric potentials to a level that can be processed (a few thousands of times), a bandpass filter to let a signal of a major frequency band of the myoelectric potentials only pass through, and a full-wave rectifier circuit. The preprocessing circuit 22 further includes an AD converter on the output side to enable digital-processing of the myoelectric-potential signals.

The movement measurement unit 30 includes a required number of imaging elements 311 to detect a light-emitting element to emit a specific color or the markers 8 having a surface treated so as to react to a specific color, for example, for an optical tracking system such as the motion capture as stated above, a position detection circuit 31 to detect imaging signals from the imaging elements 311, and a preprocessing circuit 32 to perform predetermined preprocessing to the detected imaging signals. The imaging elements 311 detect a change in position of the markers 8 in a required area. The movement measurement unit 30 may be such an apparatus to measure a position optically as well as a well-known instrument made up of a magnetic generator and a magnetic sensor that can detect the three-dimensional position and direction.

The signal processing unit 10 includes a microcomputer having a CPU, to which a ROM 11 to store a processing program for signal processing according to the present invention, a RAM 12 to temporarily store data being processed, a manipulation unit 13 including a numeric keypad or a mouse to issue a required command, and an external memory 14 to store data on a musculoskeletal model of a human body and other required data are connected. The data on a musculoskeletal model of a human body may be stored in the ROM 11 or the RAM 12. To the signal processing unit 10, a display unit 15 also is connected. The display unit 15 includes a display processing unit 151 and the monitor 152. The monitor 152 is for checking of input information from the manipulation unit 13 or to display a processing result, and is to display an image taken by a camera 40. The display processing unit 151 performs the processing to associate a processing result at the processing unit 10 with an image from the camera 40 for displaying. The display processing unit 151 may include a function unit executed in accordance with a display processing program in the signal processing unit 10 and a unit making up hardware.

The CPU of the signal processing unit 10 executes a processing program read from the ROM 11 to the RAM 12, thus functioning as a myoelectric-potential measurement processing unit 101 to periodically execute measurement processing of myoelectric potentials, a movement measurement processing unit 102 to periodically execute measurement processing of the markers 8, and an antagonistic-muscle-sum calculation unit 103, an antagonistic-muscle-ratio calculation unit 104 and a Jacobian matrix calculation unit 105 to execute pre-preparation processing based on the signals obtained from the myoelectric-potential measurement processing unit 101 and the movement measurement processing unit 102. Based on the results of the pre-preparation processing, the CPU of the signal processing unit 10 functions as a muscle synergy calculation unit 106, an equilibrium-point calculation unit 107 and a stiffness-ellipse calculation unit 108 as well.

The myoelectric-potential measurement processing unit 101 calculates EMG in terms of % MVC as described later. The movement measurement processing unit 102 calculates the distance between the markers and/or the joint angles as stated above based on the detection positions of the markers 8. The antagonistic-muscle-sum calculation unit 103 executes Mathematical Expression (1) in [Mathematical 1] as stated above, and the antagonistic-muscle-ratio calculation unit 104 executes Mathematical Expression (2) in [Mathematical 1] as stated above. The Jacobian matrix calculation unit 105 executes Mathematical Expression (3) in [Mathematical 1] as stated above. In Mathematical Expression (3), the Jacobian matrix $J_x(\theta)$ associates (maps) the hand velocity and the joint velocity. The vector x represents the hand position.

The muscle synergy calculation unit 106 executes Mathematical Expression (4) in [Mathematical 2].

[Mathematical 2]

$$< \text{Muscle synergy extraction} > \qquad (4)$$

Let that the position of an operating point represented
on the polar coordinate system is $p = (\rho, \phi)^T$,
and the antagonistic muscle ratio vector is $r = (r_1, r_2, r_3)^T$,
the following expressions hold between these variables.

$$\dot{p} = J_r(\theta_2, s)\dot{r}$$

where $\theta_2$ denotes the elbow joint angle,
$s$ denotes the antagonistic muscle sum vector,
$s = (s_1, s_2, s_3)^T$, and the details of $J_r(\theta_2, s)$ are as follows:

$$J_r(\theta_2, s) = \text{diag}\left(cL \sin\frac{\theta_2}{2}, c\right)\left(q_2(s), q_1(s) + \frac{1}{2}q_2(s)\right)^T$$

$$q_1(s) = (1 - s_{23}, s_{23}, -s_{23})^T$$

$$q_2(s) = (-s_{12}, s_{12}, 1 - s_{12})^T$$

$$s_{12} = \frac{s_1 s_2}{s_1 s_2 + s_2 s_3 + s_3 s_1}$$

$$s_{23} = \frac{s_2 s_3}{s_1 s_2 + s_2 s_3 + s_3 s_1}$$

Herein $c$ is a constant representing characteristics of muscles,
$L$ denotes link length of upper arm and
forearm. Based on these $q_1(s)$, $q_2(s)$, muscle synergy
vectors can be obtained by the following expressions.

$$\begin{cases} u_\rho(s) = \dfrac{q_2(s)}{|q_2(s)|} \\ u_o(s) = \dfrac{q_1(s) + \dfrac{1}{2}q_2(s)}{\left|q_1(s) + \dfrac{1}{2}q_2(s)\right|} \\ u_{\rho \times o}(s) = \dfrac{u_\rho(s) \times u_o(s)}{|u_\rho(s) \times u_o(s)|} \end{cases}$$

According to a muscle-synergy extraction method based on a musculoskeletal model ("Extraction of muscle coordination patterns common to various upper-limb movements of a human" the 31th Annual Conference of the Robotics Society of Japan Conference Paper collection, 2F2-03, Tokyo Metropolitan University, Sep. 4, 2013), the hand equilibrium-point velocity $p'=(\rho',\phi')^T$ on the polar coordinate system is calculated based on the antagonistic muscle ratio $r_i$ (i=1, 2, 3) and the antagonistic muscle sum $s_i$ (i=1, 2, 3) in the three-paired six-muscle model shown in FIG. 2B. Herein, $u_\rho(s)$ and $u_\phi(s)$ represent synergy vectors in the radial direction and the deflection-angle direction, respectively, and $u_\rho \times_\phi(s)$ represents a synergy vector in the Null direction.

The equilibrium-point calculation unit. 107 executes Mathematical Expression (5) in [Mathematical 3].

[Mathematical 3]

$$< \text{Estimation of equilibrium point} > \qquad (5)$$

Synergy scores of muscle synergies
can be obtained by the following expressions.

$$\begin{cases} w_\rho(s, r) = u_\rho(s) \cdot (r - \bar{r}) \\ w_\varphi(s, r) = u_\varphi(s) \cdot (r - \bar{r}) \\ w_{\rho \times \varphi}(s, r) = |u_{\rho \times \varphi}(s) \cdot (r - \bar{r})| \end{cases}$$

Factors $k\rho, k\phi$ for range regulation and offsets $\rho 0$,
$\phi 0$ are added to synergy scores $w\rho(s, r), w\phi(s, r)$,
thus estimating equilibrium-point position($\rho, \phi$).

$$\begin{cases} \rho = k_\rho w_\rho(s, r) + \rho_0 \\ \phi = k_\varphi w_\varphi(s, r) + \phi_0 \end{cases}$$

In [Mathematical 3], synergy scores are defined as the inner products of the synergy vectors $u_\rho(s)$, $u_\phi(s)$ and $u_\rho \times u_\phi(s)$ and variation vectors $r - r^-$ of the antagonistic muscle ratio r from the average $r^-$. Based on these relationships, the hand equilibrium point on the polar coordinate system and the antagonistic muscle ratio have the relationship of Mathematical Expression (5). Note here that the synergy score in the Null direction is evaluated for the magnitude only. The equilibrium point position is obtained by adjusting the ranges so that both of $u_\rho(s) \cdot (r - r^-)$ and $u_\phi(s) \cdot (r - r^-)$ agree with their actual measured values of the radius and the deflection angle during the resting states before and after the movement, calculating $\rho$ and $\phi$, and then transforming them into x-y space while setting so that $x = -\rho \cos \phi$ and $y = \rho \sin \phi$.

The stiffness-ellipse calculation unit 108 executes a method for estimating a stiffness ellipse 1 shown in Mathematical Expression (6) in [Mathematical 4], or a method for estimating a stiffness ellipse 2 shown in Mathematical Expression (8).

[Mathematical 4]

$$< \text{Estimations of stiffness ellipse 1} > \qquad (6)$$

Joint stiffness matrix $K_\theta^{emg\_s}(s)$ is obtained by the following
expression based on antagonistic muscle sum $s_i$,
where $k_s$ denotes weighting factor.

$$K_\theta^{emg\_s}(s) = k_s \begin{pmatrix} s_1 + s_2 & s_2 \\ s_2 & s_2 + s_3 \end{pmatrix}$$

At this time,
stiffness matrix $K_x^{emg\_s}(\theta, s)$ of the operating point can be
obtained by the following expression based on joint
stiffness matrix $K_\theta^{emg\_s}(s)$ and Jacobian matrix $J_x(\theta)$.

$$K_x^{emg\_s}(\theta, s) = (J_x(\theta)^T)^{-1} K_\theta^{emg\_s}(s) J_x(\theta)^{-1}$$

-continued

< Estimations of stiffness ellipse 2 > (7)
Based on antagonistic muscle
  sum $s_i$ and synergy score $w_{\rho \times \varphi}(s, r)$,
  joint stiffness matrix $K_\theta^{emg\_s+n}(s, r)$ is obtained
  by the following expression,
  where $k_s, k_n$ denote weighting factors.

$$K_\theta^{emg\_s+n}(s, r) = k_s \begin{pmatrix} s_1 + s_2 & s_2 \\ s_2 & s_2 + s_3 \end{pmatrix} + k_n w_{\rho \times \varphi}(s, r) \begin{pmatrix} 1 & 1 \\ 1 & 1 \end{pmatrix}$$

At this time, (8)
stiffness matrix $K_x^{emg\_s+n}(\theta, s, r)$ of the operating point can be
  obtained by the following expression based on joint
  stiffness matrix $K_\theta^{emg\_s+n}(s, r)$ and Jacobian matrix $J_x(\theta)$.

$$K_x^{emg\_s+n}(\theta, s, r) = (J_x(\theta)^T)^{-1} K_\theta^{emg\_s+n}(s, r) J_x(\theta)^{-1}$$

Figure 6:
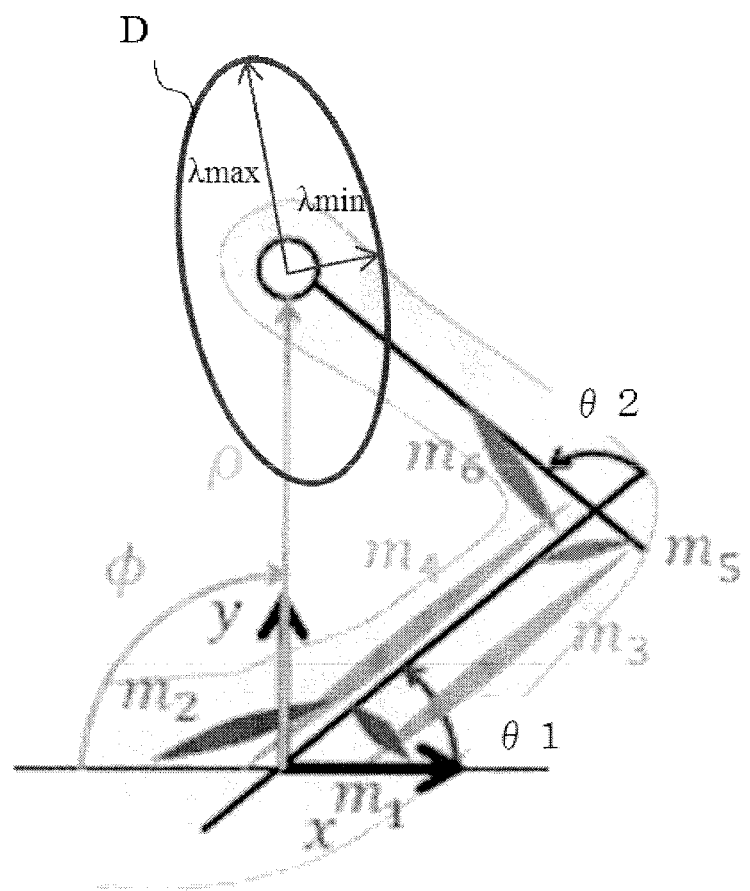
FIG. 6 describes a method for calculating a stiffness ellipse geometrically.

In the method for estimating a stiffness ellipse 1 in Mathematical Expression (6), $w_{\rho \cdot \varphi}(s,r)$ relating to the Null component at the equilibrium-point position is not involved, whereas in the method for estimating a stiffness ellipse 2 in Mathematical Expression (8), $w_{\rho \times \varphi}(s,r)$ relating to the Null component at the equilibrium point position is involved as in Mathematical Expression (7). The stiffness ellipse D shown in FIG. 6 is displayed in an overlapping manner by associating the estimation result with the operating point, where λmax denotes the direction and the length of the major axis and λmin denotes the direction and the length of the minor axis. The length of these axes indicates the difficulty in moving of the operating point (the magnitude of an external force required to displace the operating point in each direction by a predetermined amount).

A driving robot 50 includes a plurality of actuators to move required parts of a mechanism, for example, which is made up of McKibben-type artificial muscles, for example, enabling adjustment of air pressure in accordance with an electrical signal so as to expand or contract a pneumatic rubber tube, and receives a signal in accordance with the feature amounts for operation. The actuators are not limited to the McKibben-type artificial muscles, which may be an electromechanical conversion element that performs a conversion into a mechanical movement based on an electrical signal or another force converted from an electrical signal, such as an electromagnetic solenoid, a piezoelectric element or a motor. When a control target is a musculoskeletal robot having an artificial-muscle arm, e.g., an upper-limb musculoskeletal robot, a mechanism to create an artificial muscle motor command to implement a target hand movement is required similarly to the case of a human body. When a robot on the slave-machine side is controlled in accordance with an output signal from the master side that is a human body (a so-called master-slave system), since a human and a robot have different muscle characteristics and structures, feature amounts obtained from the results of measurement of myoelectric potentials of a human in real time are transformed into the antagonistic muscle ratio and the antagonistic muscle sum for the robot.

Figure 7:
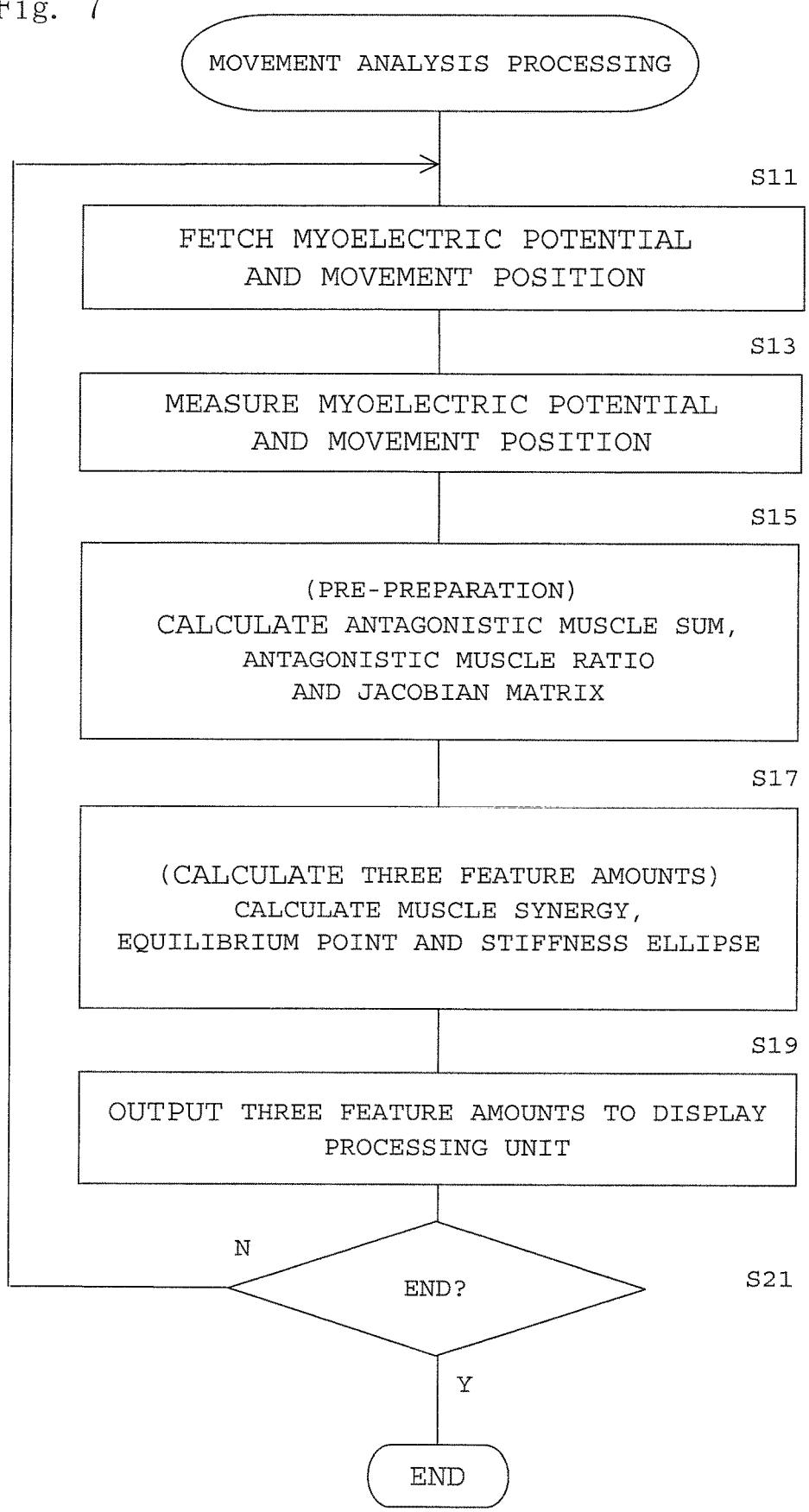
FIG. 7 is a flowchart showing one example of the procedure for movement analysis processing.

FIG. 7 is a flowchart showing the procedure for movement analysis processing. Firstly, detection signals of myoelectric potentials and signals of movement positions are fetched from the myoelectric potential measurement unit 20 and the movement measurement unit 30 (Step S11), and the processing of measuring myoelectric potentials and the processing of measuring movement positions or the like are executed based on these signals (Step S13). Next, preprocessing is executed based on the measured myoelectric potential signals and signals on movement positions or the like (Step S15). That is, values of the antagonistic muscle sum and the antagonistic muscle ratio and a Jacobian matrix are calculated in accordance with Mathematical Expressions (1) to (3).

Subsequently, based on the information obtained in the pre-preparation, three feature amounts are calculated (Step S17). That is, values of the muscle synergies, the equilibrium point and the stiffness ellipse are calculated. Then, these three feature amounts are output to the display processing unit 151 (Step S19). Next, a determination is made whether the processing ends or not (Step S21), and if it ends, the processing exits from this flow. If it does not end, the process returns to Step S11 to repeat similar processing.

Figure 8:
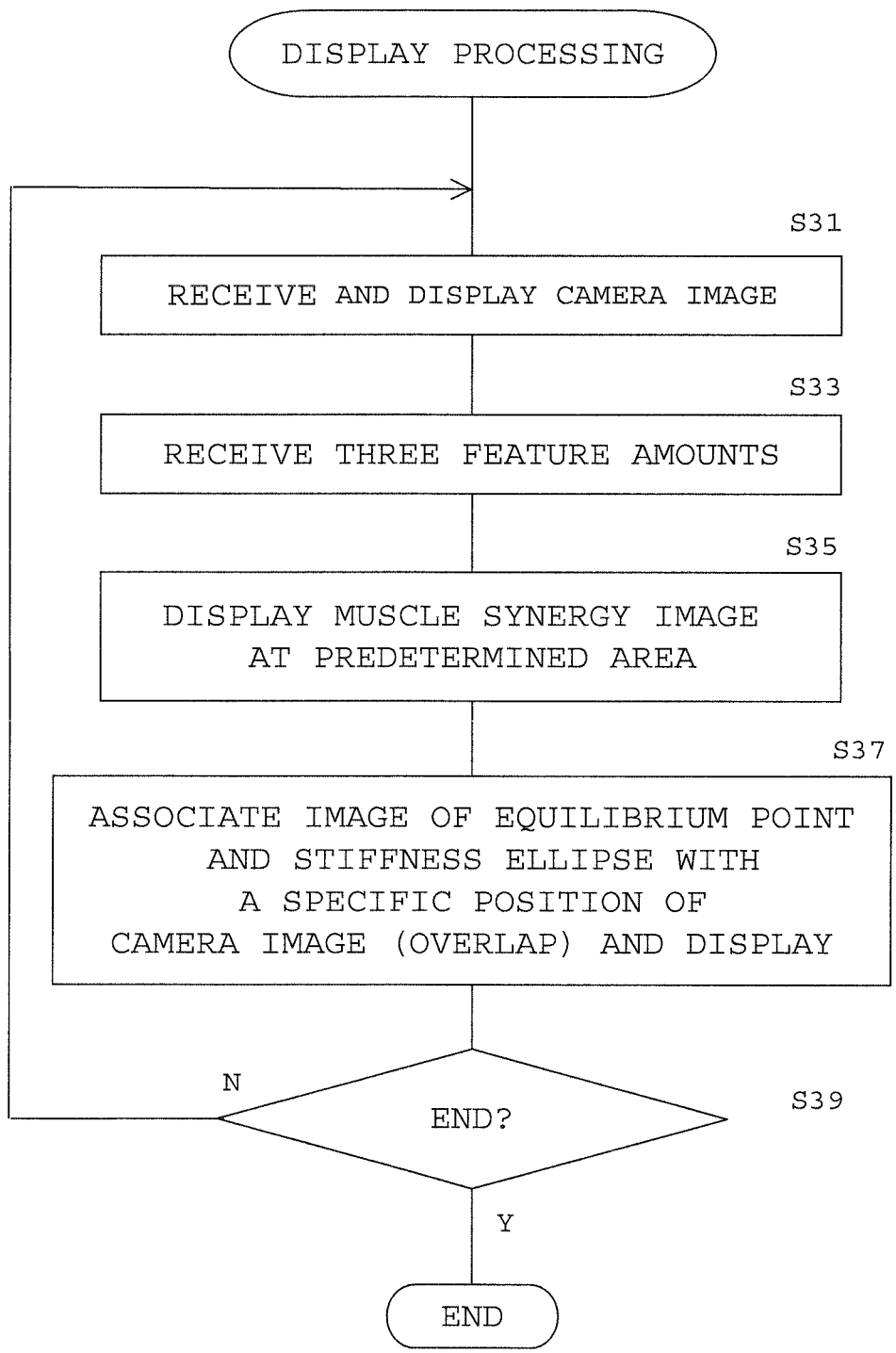
FIG. 8 is a flowchart showing one example of the procedure of display processing.

FIG. 8 is a flowchart showing the procedure of display processing. Firstly, an image taken by the camera is received, and the received image is displayed on the monitor 152 (Step S31). Next, when the three feature amounts are received (Step S33), values of the muscle synergies are represented on a predetermined diagram and are displayed at a predetermined area on the monitor 152 (Step S35). Then, the values of the equilibrium point and the stiffness ellipse are transformed into a predetermined figure (see FIGS. 1 and 6) and are displayed at a predetermined area on the monitor 152 (Step S37). Next, a determination is made whether the processing ends or not (Step S39), and if it ends, the processing exits from this flow. If it does not end, the process returns to Step S31 to repeat similar processing. The display processing in FIG. 8 may be processed with the computer of the signal processing unit 10.

The following describes an example of experiment.

Humans control a redundant musculoskeletal system appropriately so as to interact with the environment flexibly, thus implementing various movements. Many researchers have been trying to explain the mechanism of such control. Especially the adjustment of stiffness is one of the important factors to understand the movement strategy of humans. Any finding, however, has not been shown yet to integrate these control rules with the adjustment mechanism of stiffness. For this issue, the present inventors focus on muscle pairs (pairs of antagonistic muscles) disposed around a joint in an antagonistic manner and defines the ratio of EMG between a pair of antagonistic muscles as an antagonistic muscle ratio and the sum of EMG of a pair of antagonistic muscles as an antagonistic muscle sum (see Patent Document 2, although this document refers to an antagonistic muscle sum as muscle activity). The antagonistic muscle ratio contributes to the adjustment of a joint equilibrium point and the antagonistic muscle sum contributes to the adjustment of joint stiffness, and therefore the antagonistic muscle ratio and the antagonistic muscle sum can be said as the concepts to associate the coordination, the joint equilibrium point and the joint stiffness of a pair of antagonistic muscles.

Then the following describes an experiment to find the mechanism to adjust the hand stiffness during a movement based on the assumption of muscle synergies. The experiment includes measurement of EMG and hand stiffness during a reaching movement, extraction of muscle synergies based on the concepts of antagonistic muscle ratio and antagonistic muscle sum and a musculoskeletal model, and (1) comparison with the hand stiffness estimated based on the extracted muscle synergies with the hand stiffness calculated by the conventional techniques (see Non Patent Literatures 1 and 2). Then, (2) a similarity between the equilibrium-point trajectory of hand estimated using muscle synergies extracted and the equilibrium-point trajectory of hand calculated by the conventional techniques is clarified.

EXAMPLE OF EXPERIMENT

(1) Method

(1.1) Details of the Experiment

Both of the two subjects (A, B) were male in their twenties, and were right-handers. The subjects were asked to be seated so that their right shoulder was located in front of the manipulator 3, and as shown in FIG. 2A, both of the shoulders were fixed to the backrest of the chair. The muscles to be examined were three-paired six muscles (one pair of them was a bi-articular muscle pair) playing a major role in the upper-limb movement in a horizontal plane, and FIG. 2B shows the definitions of the muscles to be examined and the coordinate system.

The forearm and the upper arm were suspended from the ceiling to cancel the gravity. The wrist joint of the right arm was fixed with a cast made of plastic, and the laser pointer 4 and the forward end of the manipulator 3 (PHANTOM Premium 3.0/6DOF, produced by SensAble Technologies, sampling rate: 100 [Hz]) were fixed to the hand. On the desk, a sheet 5 was placed, on which the direction and the distance of the movement were shown, so as to allow the subject to visually check the position of the hand in real time with the laser pointer 4. The markers 8 for an optical tracking system (OptiTrack, produced by NaturalPoint Inc., sampling rate: 100 [Hz]) were fixed at the center of joints of the left shoulder, the right shoulder and the right elbow and immediately above the laser pointer 4 at the right hand. EMG was measured at 1,000 [Hz] using a myoelectric-potential acquisition apparatus and a biological amplifier (WEB-5000, Nihon Koden Corp.) as well as an AD converter (PowerLab, AD Instruments Inc.). Kinematics data obtained from the tracking system, kinetics (force) data generated by the manipulator 3 and EMG data obtained from the myoelectric-potential acquisition apparatus were measured in synchronized manner for finding the mechanism of adjustment of the equilibrium point and the stiffness at the operating point.

During a reaching movement on the horizontal plane, the start point was set at (−0.2, 0.45) [m], and the goal point was set at (0.2, 0.45) [m]. The start point and the goal point were within the range where the subjects successfully performed a natural movement. Before the reaching movement, the subjects were asked stay at the starting point for 1 [s], then to perform a reaching movement in 1 [s] and stay at the goal point for 1 [s], which was 1 trial. Beep sounds were issued five times at "1 [s] before the movement", "0.5 [s] before the movement", "starting of the movement", "end of the movement" and "1 [s] after the movement" to cue the movement. The interval time between trails was set at random within 2±0.5 [s].

Perturbations for stiffness measurement were given at one of the five timings in total including the immediately before the reaching movement (0.9 [s] after the first beep sound), the timings when the hand passed through ¼, 2/4, and ¾ of the path and the immediately before the end of the reaching movement (1.9 [s] after the first beep sound), and the timings were selected at random. The duration of the perturbations was short (0.2 [s]). Perturbations were given in eight directions at intervals of 45 [deg] from the x-axis direction, and the order of perturbations given in these directions was set at random. One set of the measurement includes 40 trials (five timings and eight directions), and eight sets of this were measured. The magnitude of perturbations was set at 6 [N] or 8 [N] depending on the physique of the subject. The subjects were asked to perform 40 trials of the reaching movement without perturbations as well.

(1.2) Data Analysis

(1.2.1) EMG Data

EMG data was through a bandpass filter at 10-450 [Hz], was then rectified, and was smoothed with a 5 [Hz] lowpass filter, and then was transformed to be % MVC using the values at the Maximum Voluntary Contraction (MVC) and was averaged. The resultants were $m_i$ (i=1, 2, ... 6). The antagonistic muscle ratios and the antagonistic muscle sums defined using mi and their functions are shown as the list in FIG. 3.

(1.3) Extraction of Muscle Synergies and Estimation of Equilibrium-Point Trajectory According to a method for extracting muscle synergies based on a musculoskeletal model proposed by the present inventors, the velocity $p'=(\rho', \phi')^T$ of hand equilibrium point, which is represented on the polar coordinate system, in the three-paired six-muscle model shown in FIG. 2B is given by Mathematical Expression (9) based on the velocity $r'=(r'_1, r'_2, r'_3)^T$ of the antagonistic muscle ratio and the antagonistic muscle sum $s_i$ (i=1, 2, 3). In this experiment, the link lengths of the upper arm and the forearm were assumed as the same for the sake of ease.

[Mathematical 5]

$$\dot{p} = J_r(\theta_2, s)\dot{r} \qquad (9)$$

where $$\dot{p} = (\dot{\rho}, \dot{\phi})^T$$

$$\dot{r} = (\dot{r}_1, \dot{r}_2, \dot{r}_3)^T$$

$$J_r(\theta_2, s) = \mathrm{diag}\left(cL\sin\frac{\theta_2}{2}, c\right)\left(q_2(s), q_1(s) + \frac{1}{2}q_2(s)\right)^T$$

and

[Mathematical 6]

$$\begin{cases} q_1(s) = (1 - s_{23}, s_{23}, -s_{23})^T \\ q_2(s) = (-s_{12}, s_{12}, 1 - s_{12})^T \\ s_{12} = \dfrac{s_1 s_2}{s_1 s_2 + s_2 s_3 + s_3 s_1} \\ s_{23} = \dfrac{s_2 s_3}{s_1 s_2 + s_2 s_3 + s_3 s_1} \end{cases} \qquad (10)$$

Herein c denotes a constant that represents the characteristics of a muscle, L denotes a link length, and θ2 denotes the elbow joint angle. These Mathematical Expressions indicate that the velocity at the hand equilibrium point can be estimated by projection of the velocity $r'=(r'_1, r'_2, r'_3)^T$ of the antagonistic muscle ratio to the vector space $q_2 \times (q_1 + q_2/2)$ (formed by combining the antagonistic muscle sums). Based on this, base vectors in the radial direction, the deflection-angle direction and the direction orthogonal to the radius and the deflection angle were found. The result was as in Mathematical Expression (11).

[Mathematical 7]

$$\begin{cases} u_\rho(s) = \dfrac{q_2(s)}{|q_2(s)|} \\ u_\varphi(s) = \dfrac{q_1(s) + \dfrac{1}{2}q_2(s)}{\left|q_1(s) + \dfrac{1}{2}q_2(s)\right|} \\ u_{\rho\times\varphi}(s) = \dfrac{u_\rho(s) \times u_\varphi(s)}{|u_\rho(s) \times u_\varphi(s)|} \end{cases} \quad (11)$$

These base vectors indicate distribution of antagonistic muscle ratio vector into the radial and the deflection-angle directions, and therefore $u_\rho(s)$ and $u_\varphi(s)$ were set as synergy vectors in the radial and the deflection-angle directions, respectively, and $u_{\rho\times\varphi}(s)$ was set as a synergy vector in the Null direction. The inner products of these synergy vectors and variation vectors $r - \bar{r}$ of the antagonistic muscle ratio $r$ from the average $\bar{r}$ were defined as synergy scores. Based on these relationships, it was found that the hand equilibrium point on the polar coordinate system and the antagonistic muscle ratio have the relationship as shown in Mathematical Expression (12).

[Mathematical 8]

$$\begin{cases} \rho \propto u_\rho(s) \cdot (r - \bar{r}) \\ \phi \propto u_\varphi(s) \cdot (r - \bar{r}) \end{cases} \quad (12)$$

Herein the ranges were adjusted so that both of $u_\rho \cdot (r - \bar{r})$ and $u_\varphi \cdot (r - \bar{r})$ agree with their actual measured values in radius and deflection angle during the resting states before and after the movement, ρ and φ were calculated, and then they were transformed into x-y space while setting so that $x_{eq}^{emg} = (-\rho \cos \phi, \rho \sin \phi)$.

Note here that the synergy score in the Null direction was evaluated for the magnitude only.

(1.3.1) Estimation of Hand Stiffness Based on EMG Data

The past study (the article as stated above) shows that a joint stiffness matrix $K_\theta^{emg\_s}(s)$ can be represented using the antagonistic muscle sum $s_i$ (i=1, 2, 3) based on the musculoskeletal model as in Mathematical Expression (13).

[Mathematical 9]

$$K_\theta^{emg\_s}(s) = k_s \begin{pmatrix} s_1 + s_2 & s_2 \\ s_2 & s_2 + s_3 \end{pmatrix} \quad (13)$$

Herein $k_s$ is a constant to transform an antagonistic muscle sum as a dimensionless number into the joint stiffness. In order to verity the hypothesis that the synergy vector in the Null direction regulates the magnitude and the direction of stiffness especially under a dynamic situation, the synergy score $w_{\rho\times\varphi}(s,r) = u_{\rho\times\varphi}(s) \cdot (r - \bar{r})$ in the Null direction was added to each component of the joint stiffness matrix $K_\theta^{emg\_s}(s)$, which was set as a joint stiffness matrix $K_\theta^{emg\_s+n}(s,r)$ estimated from the EMG data as shown in Mathematical Expression (14). The value of $k_n$ was set at 200 (Nm/rad experimentally.

[Mathematical 10]

$$K_\theta^{emg\_s+n}(s, r) = k_s \begin{pmatrix} s_1 + s_2 & s_2 \\ s_2 & s_2 + s_3 \end{pmatrix} + k_n w_{\rho\times\varphi}(s, r) \begin{pmatrix} 1 & 1 \\ 1 & 1 \end{pmatrix} \quad (14)$$

The stiffness matrix $K_\theta^{emg\_s+n}(s,r)$ in a joint space was transformed into stiffness $K_x^{emg\_s+n}(\theta,s,r)$ in a task space by Mathematical Expression (15), which was set as an hand stiffness matrix estimated from the EMG data.

[Mathematical 11]

$$K_x^{emg\_s+n}(\theta,s,r) = (J_x(\theta)^T)^{-1} K_\theta^{emg\_s+n}(s,r) J_x(\theta)^{-1} \quad (15)$$

Herein $J_x(\theta)$ is a Jacobian matrix to associate the hand velocity with the joint velocity.

(1.3.2) Estimation of Hand Stiffness and Equilibrium-Point Trajectory by a Perturbation Method The movement of the hand was measured in a state where two of the reaching movement (the movement that the subject originally intended to perform) and of the displacement by perturbations were mixed. In order to cancel the influences from the direction of the perturbations by the manipulator 3, the timing when the perturbations were given, and the presence or not of the perturbations from the reaching movement, the average joint angle vector $\theta(t) = (\theta_1(t), \theta_2(t))^T$ of all data was set as the reaching movement.

Meanwhile, as shown in Mathematical Expression (16), the displacement due to the perturbations, $\delta\theta(t) = (\delta\theta_1(t), \delta\theta_2(t))^T$ was set by subtracting the perturbation-direction average vector $\theta_{sav}(t)$ of the displacement after the starting of the perturbations from the displacement vector $\theta_{s,i}(t)$ after the starting of the perturbations.

[Mathematical 12]

$$\begin{cases} \theta_{s,i}(t) = \theta_i(t) - \theta_i(t_s) & (i = 1, 2, \ldots, 8) \\ \theta_{sav}(t) = \dfrac{1}{n}\sum_{i=1}^{n} \theta_{s,i}(t) & (n = 8) \\ \delta\theta_i(t) = \theta_{s,i}(t) - \theta_{sav}(t) \end{cases} \quad (16)$$

Herein i=1, 2, . . . 8 represents the direction of perturbations, and $t_s \leq t \leq t_s + T$. ts denotes the time when the perturbations started, and T was the duration required to move a section that was used for stiffness estimation calculation, which was set at 0.4 [s]. When the perturbations were given, a command was issued so that a certain hand force was generated at the manipulator 3, and therefore it was assumed that a certain external force was generated during the movement of the section. Mathematical Expression (17) shows this relationship.

[Mathematical 13]

$$\delta f(t) = \begin{cases} (0, 0)^T & (t < t_s) \\ f \cdot (\cos(\pi i/4), \sin(\pi i/4))^T & (t_s \leq t \leq t_s + T) \\ (0, 0)^T & (t_s + T < t) \end{cases} \quad (17)$$

The magnitude of f was set at 8 [N] for subject A and 6 [N] for subject B. These external forces were transformed into a joint space, which was set as the perturbation torque $\delta\tau(t)=J_x(\theta)_T\delta f(t)$.

Based on $\theta(t)$, $\delta\theta(t)$ and $\delta\tau(t)$, an inertia matrix $I(\theta)$, a joint viscosity matrix $D=[[D_{ss},D_{ee}]^T, [D_{es},D_{ee}]^T])$, and a joint stiffness matrix $K_\theta^{ptb}=[[K_{sa},K_{se}]^T, [K_{es},K_{ee}]^T]$ were calculated from the dynamic equation (see Hiroaki Gomi, Mitsuo Kawato, "Human arm stiffness and equilibrium-point trajectory during multijoint movement," Biological Cybernetics, vol. 76, no. 3, pp. 163-171, 1997.). Here in the hand stiffness matrix, $K_x^{ptb}(\theta)$ was found by Mathematical. Expression (18) using the joint stiffness matrix $K_\theta^{ptb}$, the Jacobian matrix $J_x(\theta)$ and the force $F_{in}$ that the arm generated at the hand, which was estimated from physical parameters calculated by the dynamic equation as stated above.

[Mathematical 14]

$$K_x^{ptb}(\theta) = (J_x(\theta)^T)^{-1}\left\{K_\theta^{ptb} + \frac{dJ_x(\theta)^T}{d\theta^T}F_{in}\right\}J_x(\theta)^{-1} \quad (18)$$

Based on the calculated joint stiffness matrix $K_\theta^{ptb}$ and joint viscosity matrix D, the equilibrium-point trajectory xhd $eq^{ptb}$ of the hand was calculated in accordance with Mathematical Expression (19).

[Mathematical 15]

$$\begin{cases} x_{eq}^{ptb} = \Phi(\theta_{eq}^{ptb}) \\ \theta_{eq}^{ptb} = \left(K_\theta^{ptb}(\theta)\right)^{-1}\left(I(\theta)\ddot{\theta} + H(\dot{\theta},\theta) + D\dot{\theta} - \tau_{ext}\right) + \theta \end{cases} \quad (19)$$

Herein $\Phi$ denotes a forward kinematics function to transform the coordinates of the joint angle into the x-y coordinates of the hand, and $I(\theta)$, $H(\theta',\theta)$ were calculated from the physical parameters obtained by the method as stated above and $\theta=(\theta_1,\theta_2)^T$. D and $K_\theta^{ptb}$ were calculated by linear interpolation of the values obtained for each of the five positions of the hand and by transforming them into data at 20 [Hz].

(2) Results (2.1) Antagonistic Muscle Ratio and Antagonistic Muscle Sum, and Muscle Synergy Extraction FIGS. 9A and 9B show the transition of the antagonistic muscle sum $s_i$ and the antagonistic muscle ratio $r_i$ obtained from the experiment on Subject A. FIG. 9A shows the antagonistic muscle sum $s_i$ and FIG. 9 shows the antagonistic muscle ratio $r_1$. FIGS. 10A and 10B show synergy vectors $u_\rho(s)$, $u_\phi(s)$, $u_{\rho\times\phi}(s)$ in the radial, the deflection-angle and the Null directions, respectively, obtained based on these antagonistic muscle sum $s_i$ and the antagonistic muscle ratio $r_i$, and their synergy scores $u_\rho(s)\cdot(r-r^-)$, $u_\phi(s)\cdot(r-r^-)$, $|u_{\rho\times\phi}(s)\cdot(r-r^-)|$. FIG. 10A shows data on Subject A, and FIG. 10B shows data on Subject B. In the drawing, columns showing the synergy vectors on the left correspond to $r_1$, $r_2$ and $r_3$, respectively, from the left. A similar result can be found between Subjects A and B.

(2.2) Joint Stiffness and Hand Stiffness

Figure 12A:
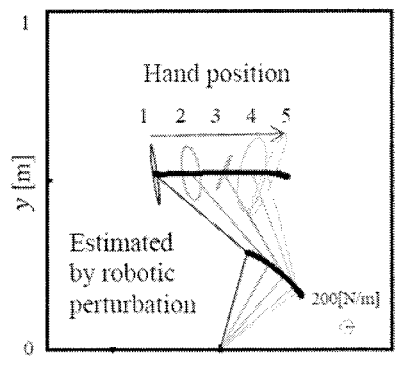
FIGS. 12A, 12B and 12C show hand stiffness that is obtained by transforming the joint stiffness obtained by a perturbation method, and hand stiffness estimated from the antagonistic muscle sum and synergy score in the Null direction, where
Figure 12B:
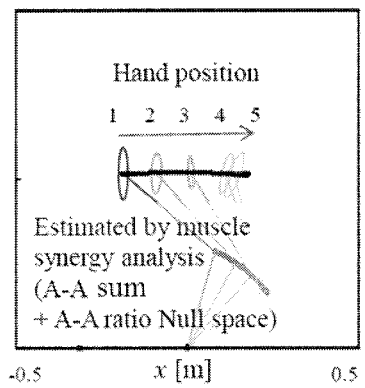
Figure 12C:
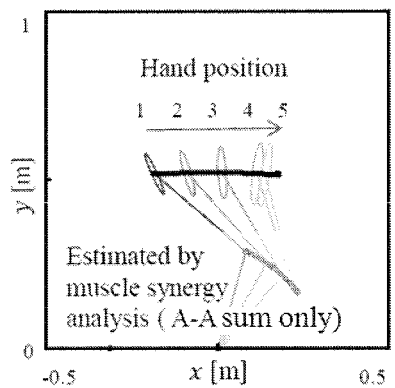

FIGS. 11A and 11B show joint stiffness calculated by a perturbation method. FIG. 11A shows data on Subject A, and FIG. 11B shows data on Subject B. Next, FIGS. 12A, 12B and 12C show hand stiffness that is obtained by transforming the joint stiffness obtained by the perturbation method, and hand stiffness estimated from the antagonistic muscle sum and synergy score in the Null direction. FIG. 12A shows the characteristics obtained by the perturbation method, and FIG. 12B shows the characteristics obtained by the estimation method this time.

[Mathematical 16]

$$K_x^{emg\_s}(\theta,s) = (J_x(\theta)^T)^{-1}(K_\theta^{emgs}(s))J_x(\theta)^{-1} \quad (20)$$

For comparison, FIG. 12C shows the characteristics of hand stiffness that was obtained without adding the synergy score in the Null direction (shown in Mathematical Expression (20) in [Mathematical 16]).

(2.3) Trajectory and Velocity of Equilibrium Point at Hand

FIGS. 13A and 13B show the equilibrium-point trajectory $x_{eq}^{ptb}$ of the hand calculated based on the joint stiffness matrix $K_\theta^{ptb}$ or the like, the equilibrium-point trajectory $x_{eq}^{emg}$ of the hand estimated from the muscle synergy scores, and the magnitude of their tangential velocities $|x'_{eq}^{ptb}|$, $|x'_{eq}^{emg}|$. FIG. 13A shows the characteristics obtained by the perturbation method, and FIG. 13B shows the characteristics obtained by the estimation method this time.

(3) Discussion (3.1) Extracted Muscle Synergies

As shown in FIGS. 10A and 10B on the left, muscle synergy vectors extracted by the present analysis method highly agreed between the two subjects (the inner products 0.94±0.02). This shows that this muscle-synergy extraction method hardly reflects individual differences between the subjects, and in other words, this method has a high degree of generality.

Further FIGS. 10A and 10B on the left shows that, for the synergy vector $u_\rho(s)$ in the radial direction, the bi-articular muscle pair supported elbow joint extension when the subject moved their hands in the positive radial direction. For the synergy vector $u_\square(s)$ in the deflection-angle direction, it is shown that the mono-articular muscle pair of the shoulder and the bi-articular muscle pair of the shoulder and the elbow cooperated to act on the shoulder joint movement when the subject moved their hands in the positive deflection-angle direction, while the mono-articular muscle pair of the elbow did not act thereon.

Meanwhile the synergy vector $u_{\rho\times\phi}(s)$ in the Null direction shows the antagonism state of the mono-articular muscle pairs of the shoulder and the elbow and the bi-articular muscle pair of the shoulder/elbow. It means that even when the antagonistic muscle ratio vector r changes in the Null direction, the equilibrium point of the hand does not change. On the contrary, as shown in FIGS. 10A and 10B on the right, the synergy scores in the Null direction changed greatly immediately after the starting of the reaching movement and immediately before the end. This tendency was observed common to the subjects. This shows that the synergy vector in the Null direction is a muscle synergy having a role other than the regulation of the equilibrium point of the hand.

(3.2) Hand Stiffness, Antagonistic Muscle Sum and Synergy Score in Null Direction As shown in FIG. 12A, the hand stiffness obtained by the perturbation method increased in their values immediately after the start and immediately before the end of the movement, and decreased in the middle of the movement.

The stiffness ellipse in the middle of the movement slightly tilted from the direction connecting the shoulder and the hand, which shows that the direction of the hand stiffness changed during the movement. Such a change in the direction of the hand stiffness during the movement is common to all of the drawings. A change in the size of the elliptical shape indicating the hand stiffness during the movement also is common to FIGS. 12A and 12B.

For the antagonistic muscle sum and the synergy scores in the Null direction, they are similar to the transition of the magnitude of the hand stiffness because they had two peaks immediately after the start and immediately before the end of the movement. As shown in FIG. 12B, the hand stiffness estimated using the antagonistic muscle sum and the synergy scores in the Null direction follows the transition having a shape closer to the actual measured values than the hand stiffness ellipses estimated based on the antagonistic muscle sum only in FIG. 12C. Therefore it can be considered that synergy scores in the Null direction of the antagonistic muscle sum and the antagonistic muscle ratio greatly contribute to the regulation of the magnitude and the direction of the hand stiffness.

(3.3) Trajectory and Velocity of Equilibrium Point at Hand, and Synergy Scores in the Radial and the Deflection-Angle Directions While the velocity profile of actual hand movement had a bell shape, the velocity profile of virtual hand movement (equilibrium-point velocity) obtained based on the joint stiffness showed multiple peaks as shown in FIG. 13A. Such a multiple-peak shape was shown also in the hand equilibrium velocity estimated from the synergy scores in the radial and the deflection-angle directions (FIG. 13B). This shows that the equilibrium-point trajectory obtained from muscle synergies extracted by the present method had a feature similar to the equilibrium-point trajectory obtained from the hand stiffness. From this, it can be considered that synergy vector $u_\rho(s)$ in the radial direction and synergy vector $u_\phi(s)$ in the deflection-angle direction contribute to the regulation of the hand equilibrium point.

The analysis method and apparatus as stated above are described by way of the form where the subject moved the upper limb on the desk. The part to be moved may be a lower limb instead of the upper limb, or may be a wide range of movement including a fullbody movement where both of the upper limbs and the lower limbs are moved together. That is, the analysis method and apparatus as stated above can provide a user with a motor control strategy (depending on the level of motor learning and the individual difference) that the central nervous system selects for a wide range of movement in an objective and quantitative manner under a clear standard, and can provide them with specific means for supporting motor learning. Various examples of the movement can be assumed depending on the purpose, and the method and apparatus can be applied to learning of movements and skills of various sports and acquisition of a movement and actions other than sports. That is, when they are used for a method and an apparatus of supporting motor learning in order to establish an effective exercise or such intervention toward a target movement, feature amounts of the movement by a model person are acquired beforehand, and a learner is supported to learn the movement while referring to the feature amounts so as to bring their feature amounts to those of the model person. Alternatively, a learner may be supported to learn the movement while observing a change in their own feature amounts during each learning step.

The analysis method and apparatus as stated above can be used to a method and an apparatus to evaluate movement control for analysis of a motor control mechanism or a motor learning mechanism of a healthy person and a brain-diseased patient, for example. In one form, motor skills may be diagnosed and evaluated based on the above-stated estimated three feature amounts in accordance with a motor command from the central nervous system, and motor learning may be promoted via additional feedback. Such a form is effective in the sports field and the rehabilitation field. In this way, the three feature amounts obtained from the present analysis method can be effectively used for motor control evaluations and motor learning support.

The analysis method and apparatus can be used for an interface evaluation apparatus to design and evaluate machines, tools and environment involving physical interaction with humans.

As described above, a movement analysis apparatus according to the present invention includes: a measurement unit to periodically measure a muscle-group activity and a body movement of a person who performs a movement; and calculation means to calculate, from measurement information obtained by the measurement unit, feature amounts including a stiffness ellipse, an equilibrium point, and a muscle synergy that are base vectors describing the equilibrium point at an operating point based on a musculoskeletal model.

According to the present invention, feature amounts can be estimated analytically based on a physical model, can be estimated through algebraic calculations that do not require complicated parameter identification or a large scale apparatus, and can be dealt with uniformly under the concepts of the antagonistic muscle ratio and the antagonistic muscle sum. The three feature amounts including muscle synergies estimated can be estimated based on a physical model, and therefore the physical significance thereof can be clarified as compared with the one estimated from a neural network model or by a statistical method.

Preferably the measurement unit of the movement analysis apparatus includes a myoelectric-potential detection unit to detect myoelectric potential as the muscle activity and a movement detection unit to measure a movement of a joint as the body movement, and the calculation means includes first calculation means to calculate an antagonistic muscle ratio and an antagonistic muscle sum and second calculation means to calculate a Jacobian matrix to map a measurement portion of a body movement to the operating point based on the musculoskeletal model, and calculates the feature amounts based on the antagonistic muscle ratio and the antagonistic muscle sum, and the Jacobian matrix calculated. This configuration can be used for a complicated movement task whose stiffness ellipse and equilibrium point are technically difficult to estimate or cannot be estimated by a perturbation method. This configuration is not affected by a reflex system involved in perturbations. Further, this does not require the collection and analysis of a huge amount of data to estimate the stiffness ellipse or the equilibrium point as in a method of analyzing an electromyogram using a neural-network model, for example.

Preferably the movement analysis apparatus includes an output unit to output a calculation result. With this configuration, a motor control solution (motor command) that the central nervous system is to select to implement a desired movement based on three feature amounts can be observed from moment to moment with the output unit, such as a monitor.

Preferably the movement analysis apparatus includes an imaging unit to observe the body movement, and the output unit includes a display unit to display an image. The display unit preferably displays at least the equilibrium point and the stiffness ellipse of the feature amounts, and an image of the body movement taken by the imaging unit. With this configuration, since the calculation result can be displayed while being associated with the body image during the movement, visibility of the feature amounts can be improved.

Preferably the output unit of the movement analysis apparatus displays the equilibrium point in association with an image of the body movement. With this configuration, the position of the equilibrium point can be visually checked appropriately.

Preferably the output unit of the movement analysis apparatus displays the stiffness ellipse in association with an operating point in an image of the body movement. With this configuration, the state of the stiffness ellipse can be visually checked appropriately.

Preferably the output unit of the movement analysis apparatus includes a driving unit to give physical assistance to a target of supporting based on the feature amounts. With this configuration, the apparatus can be used in the rehabilitation field or in an interface evaluation apparatus.

REFERENCE SIGNS LIST

10 Signal processing unit (calculation means)
103 Antagonistic-muscle-sum calculation unit (first calculation means)
104 Antagonistic-muscle-ratio calculation unit (first calculation means)
105 Jacobian matrix calculation unit (second calculation means)
106 Muscle synergy calculation unit (calculation means)
107 Equilibrium-point calculation unit (calculation means)
108 Stiffness-ellipse calculation unit (calculation means)
20 Myoelectric potential measurement unit (measurement unit)
30 Movement measurement unit (measurement unit)
40 Camera (imaging unit)
15 Display unit (output unit)
50 Driving device (output unit)

The invention claimed is:

1. A movement analysis apparatus, comprising:
a memory unit to store information on a musculoskeletal model of a body;
a measurement unit comprising a first detector with an electrode, which measures myoelectric potential due to a muscle-group activity of a person who performs a specific movement which is according to a movement command from a central nervous system of the person, and a second detector with an imaging element, which periodically measures a movement of a joint due to a body movement of the person, the measurement unit storing each measuring information obtained by the first detector and the second detector in the memory unit;
a computer, which reads said each measuring information from the memory unit, and calculates, based on the musculoskeletal model, a plurality of feature amounts, including a stiffness ellipse, an equilibrium point, and a muscle synergy, the muscle synergy being a base vector which describes the equilibrium point at an operating point of the body; and
a display unit for displaying a result calculated by the computer;
wherein the computer includes a first calculation unit to calculate an antagonistic muscle ratio and an antagonistic muscle sum based on the myoelectric potential measured by the first detector, and a second calculation unit to calculate a Jacobian matrix to map a measurement portion of a body movement to the operating point based on the musculoskeletal model and the movement of the joint measured by the second detector, and calculates the feature amounts based on the antagonistic muscle ratio and the antagonistic muscle sum, and the Jacobian matrix calculated.

2. The movement analysis apparatus according to claim 1, further comprising a camera distinct from the imaging element to capture a movement image of the body movement, wherein the display unit displays the images of at least the equilibrium point and the stiffness ellipse of the feature amounts, and the movement image of the body movement taken by the camera.

3. The movement analysis apparatus according to claim 1, wherein the display unit displays the equilibrium point in association with an image of the body movement.

4. The movement analysis apparatus according to claim 1, wherein the display unit displays the stiffness ellipse in association with an operating point in an image of the body movement.

5. The movement analysis apparatus according to claim 1, further comprising a robot which gives physical assistance to a target of supporting based on the feature amounts.

6. The movement analysis apparatus according to claim 1 configured for rehabilitation of said specific movement of said person further comprising a robot which gives physical assistance to a target of supporting based on the feature amounts.

7. The movement analysis apparatus according to claim 1 configured for targeted learning of said specific movement of said person further comprising a robot which gives physical assistance to a target of supporting based on the feature amounts.

* * * * *